US009375262B2

(12) United States Patent
Reschke et al.

(10) Patent No.: US 9,375,262 B2
(45) Date of Patent: Jun. 28, 2016

(54) LIMITED USE MEDICAL DEVICES

(71) Applicant: COVIDIEN LP, Mansfield, MA (US)

(72) Inventors: Arlen J. Reschke, Longmont, CO (US);
Gary M. Couture, Longmont, CO (US);
Rebecca J. Coulson, Lyons, CO (US);
Sara E. Anderson, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 305 days.

(21) Appl. No.: 14/100,237

(22) Filed: Dec. 9, 2013

(65) Prior Publication Data

US 2014/0243811 A1    Aug. 28, 2014

Related U.S. Application Data

(60) Provisional application No. 61/770,088, filed on Feb. 27, 2013.

(51) Int. Cl.
*A61B 18/14* (2006.01)
*A61B 18/00* (2006.01)

(52) U.S. Cl.
CPC .......... *A61B 18/1445* (2013.01); *A61B 18/1442* (2013.01); *A61B 2018/00083* (2013.01); *A61B 2018/00672* (2013.01); *A61B 2018/00875* (2013.01)

(58) Field of Classification Search
CPC ........... A61B 18/1445; A61B 18/1442; A61B 18/1233; A61B 2018/0083; A61B 2018/00672; A61B 2018/00875; A61B 2018/00178; A61B 2018/00988; A61B 2019/4873

See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 08/926,869, filed Sep. 10, 1997, James G. Chandler.

(Continued)

*Primary Examiner* — Michael Peffley

(57) ABSTRACT

The present disclosure is directed to a surgical system that may include an end effector assembly configured to conduct energy through tissue to treat tissue, the end effector assembly including at least one limited-use portion, the limited-use portion configured to degrade during use, and a control system configured to monitor degradation of the limited-use portion.

9 Claims, 6 Drawing Sheets

(56) References Cited

U.S. PATENT DOCUMENTS

| | | | |
|---|---|---|---|
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| 8,522,626 B2 | 9/2013 | Woodcock | |
| 8,535,311 B2 | 9/2013 | Schall | |
| 8,546,999 B2 | 10/2013 | Houser et al. | |
| 8,579,177 B2 | 11/2013 | Beetel | |
| 2003/0208196 A1* | 11/2003 | Stone | A61B 18/14 606/41 |
| 2010/0042097 A1* | 2/2010 | Newton | A61B 18/14 606/41 |
| 2011/0306972 A1 | 12/2011 | Widenhouse et al. | |
| 2012/0205419 A1 | 8/2012 | Weir et al. | |
| 2012/0248167 A1 | 10/2012 | Flanagan et al. | |
| 2013/0046303 A1 | 2/2013 | Evans et al. | |
| 2013/0181033 A1 | 7/2013 | Shelton, IV et al. | |
| 2013/0186933 A1 | 7/2013 | Shelton, IV et al. | |
| 2013/0267950 A1 | 10/2013 | Rosa et al. | |
| 2013/0282024 A1 | 10/2013 | Blumenkranz | |
| 2013/0289558 A1* | 10/2013 | Reid, Jr. | A61B 18/1477 606/41 |
| 2013/0289559 A1* | 10/2013 | Reid, Jr. | A61B 18/1477 606/41 |
| 2013/0289560 A1 | 10/2013 | DeCarlo et al. | |
| 2014/0200580 A1* | 7/2014 | Joseph | A61B 18/1445 606/45 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |

(56) References Cited

FOREIGN PATENT DOCUMENTS

| WO | 0115614 A1 | 3/2001 |
|---|---|---|
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/040483 A1 | 4/2008 |
| WO | 2011/018154 A1 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Schmaltz et al.
U.S. Appl. No. 09/591,328, filed Jun. 9, 2000, Ryan et al.
U.S. Appl. No. 12/336,970, filed Dec. 17, 2008, Sremcich et al.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

\* cited by examiner

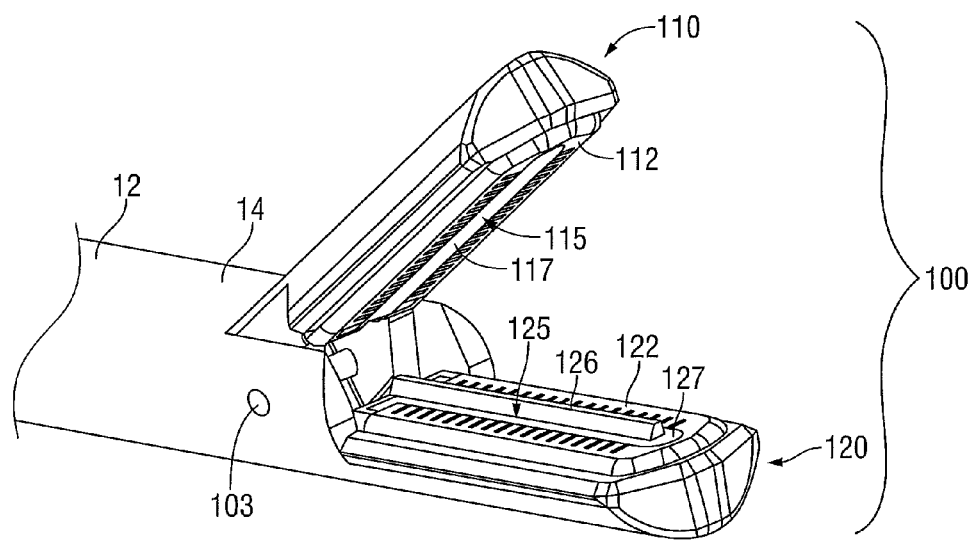
FIG. 3
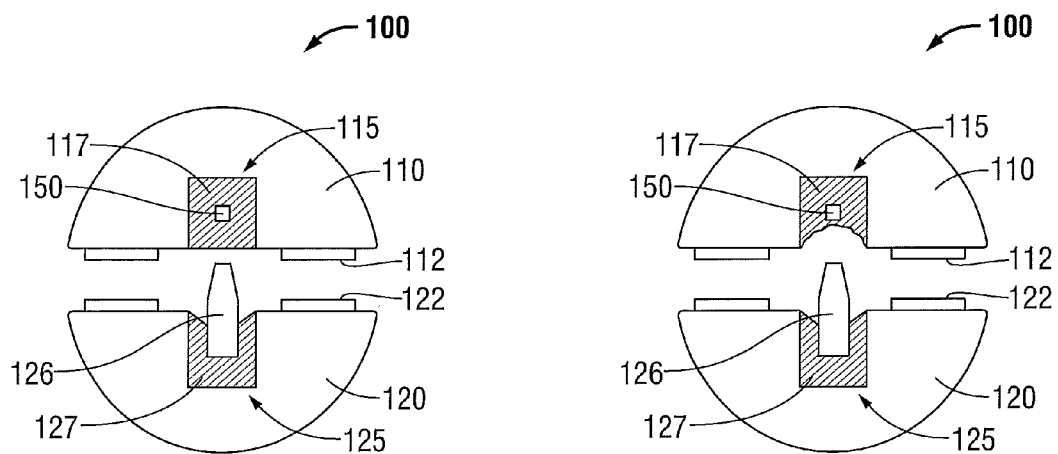
FIG. 4A  FIG. 4B

LIMITED USE MEDICAL DEVICES

CROSS REFERENCE TO RELATED APPLICATION

The present application claims the benefit of and priority to U.S. Provisional Application Ser. No. 61/770,088, filed on Feb. 27, 2013, the entire contents of which are incorporated herein by reference.

BACKGROUND

1. Technical Field

The present disclosure relates to medical devices and, more particularly, to medical devices configured for a limited number of uses and/or period of use.

2. Background of the Related Art

Certain medical devices (or components thereof) are capable of being used multiple times, and are thus referred to as reusable devices (or reusable components), while other medical devices (or components thereof) are configured for single use, and are thus referred to as disposable devices (or disposable components). Many such reusable and disposable medical devices, and/or the components thereof, are designed for a pre-determined number of uses and/or for a pre-determined usage time. Use of these devices beyond their prescribed usage time or number of uses may result in failure of the device, damage to the device or surrounds, and/or injury to the patient or clinician. On the other hand, given the rising costs of performing medical procedures, clinician's have an incentive to maximize the reuse of medical devices (or components thereof).

SUMMARY

Like reference numerals may refer to similar or identical elements throughout the description of the figures. As shown in the drawings and described throughout the following description, as is traditional when referring to relative positioning on a surgical device, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of aspects described herein.

In at least one aspect of the present disclosure, a surgical system comprises an end effector assembly configured to conduct energy through tissue to treat tissue, the end effector assembly including at least one limited-use portion, the limited-use portion configured to degrade during use, and a control system configured to monitor degradation of the limited-use portion.

In another aspect of the present disclosure, the control system includes a sensor configured to sense at least one characteristic indicative of degradation of the limited-use portion and to provide a signal representative of the at least one characteristic sensed.

In another aspect of the present disclosure, the end effector assembly includes an energizable electrode and an insulator in proximity to the energizable electrode, the limited-use portion including at least a portion of the insulator.

In another aspect of the present disclosure, the insulator is configured to degrade as a result of energy conduction therethrough or adjacent thereto.

In another aspect of the present disclosure, the control system monitors the insulator such that when the insulator erodes to a predetermined threshold, the control system inhibits energy transmission to the end effector assembly.

In another aspect of the present disclosure, when the insulator erodes sufficiently so as to short-circuit the end effector assembly, the control system inhibits energy transmission to the end effector assembly.

In another aspect of the present disclosure, the end effector assembly includes an energizable electrode, the limited-use portion including at least a portion of the electrode.

In another aspect of the present disclosure, the electrode erodes as a result of energy conduction therethrough.

In another aspect of the present disclosure, the control system monitors the electrode such that when the electrode erodes to a predetermined threshold, the control system inhibits energy transmission to the end effector assembly.

In another aspect of the present disclosure, when the electrode erodes sufficiently so as to short-circuit the end effector assembly, the control system inhibits energy transmission to the end effector assembly.

In another aspect of the present disclosure, a method of surgery comprises providing a medical device including an end effector assembly configured to conduct energy through tissue to treat tissue, the end effector assembly including at least one limited-use portion configured to degrade with use, and monitoring degradation of the at least one limited-use portion.

In another aspect of the present disclosure, the method further comprises monitoring degradation further includes sensing at least one characteristic indicative of degradation of the at least one limited-use portion.

In another aspect of the present disclosure, the method further comprises the step of inhibiting energy transmission to the end effector assembly when degradation of the at least one limited-use portion exceeds a pre-determined threshold.

In another aspect of the present disclosure, the method further comprises the step of inhibiting energy transmission to the end effector assembly when the at least one limited-use portion erodes sufficiently so as to short-circuit the end effector assembly.

In another aspect of the present disclosure, a medical device comprises an end effector assembly configured to conduct energy through tissue to treat tissue, the end effector assembly including at least one limited-use portion, the limited-use portion configured to degrade during use, wherein when the limited-use portion degrades beyond a predetermined threshold, the medical device transitions to an inoperable state.

In another aspect of the present disclosure, the limited-use portion is an electrical portion of the end effector assembly, such that when the limited-use portion degrades beyond the predetermined threshold, the end effector becomes mechanically inoperable.

In another aspect of the present disclosure, the limited use portion is an electrical component of the end effector assembly, such that when the limited-use portion degrades beyond the predetermined threshold, the end effector becomes electrically inoperable.

In another aspect of the present disclosure, the medical device further comprises a control system that transitions the medical device to the inoperable state when the limited-use portion degrades beyond a predetermined threshold.

In another aspect of the present disclosure, the limited-use portion is an electrical component of the end effector assembly, such that when the limited-use portion degrades beyond the predetermined threshold, the control device cuts an electrical supply from the end effector assembly.

In another aspect of the present disclosure, the limited-use portion is an insulator of the end effector assembly, such that when the limited-use portion degrades beyond the predetermined threshold, the end effector assembly becomes electrically inoperable.

BRIEF DESCRIPTION OF THE DRAWINGS

The above and other aspects, features, and advantages of the present disclosure will become more apparent in light of the following detailed description when taken in conjunction with the accompanying drawings in which:

FIG. 3 is a perspective view of an end effector assembly provided in accordance with this disclosure and configured for use with the medical devices of FIGS. 1 and 2;

FIG. 4A is a cross-sectional view of the end effector assembly of FIG. 3 shown in a first condition;

FIG. 4B is a cross-sectional view of the end effector assembly of FIG. 3 shown in a second condition;

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
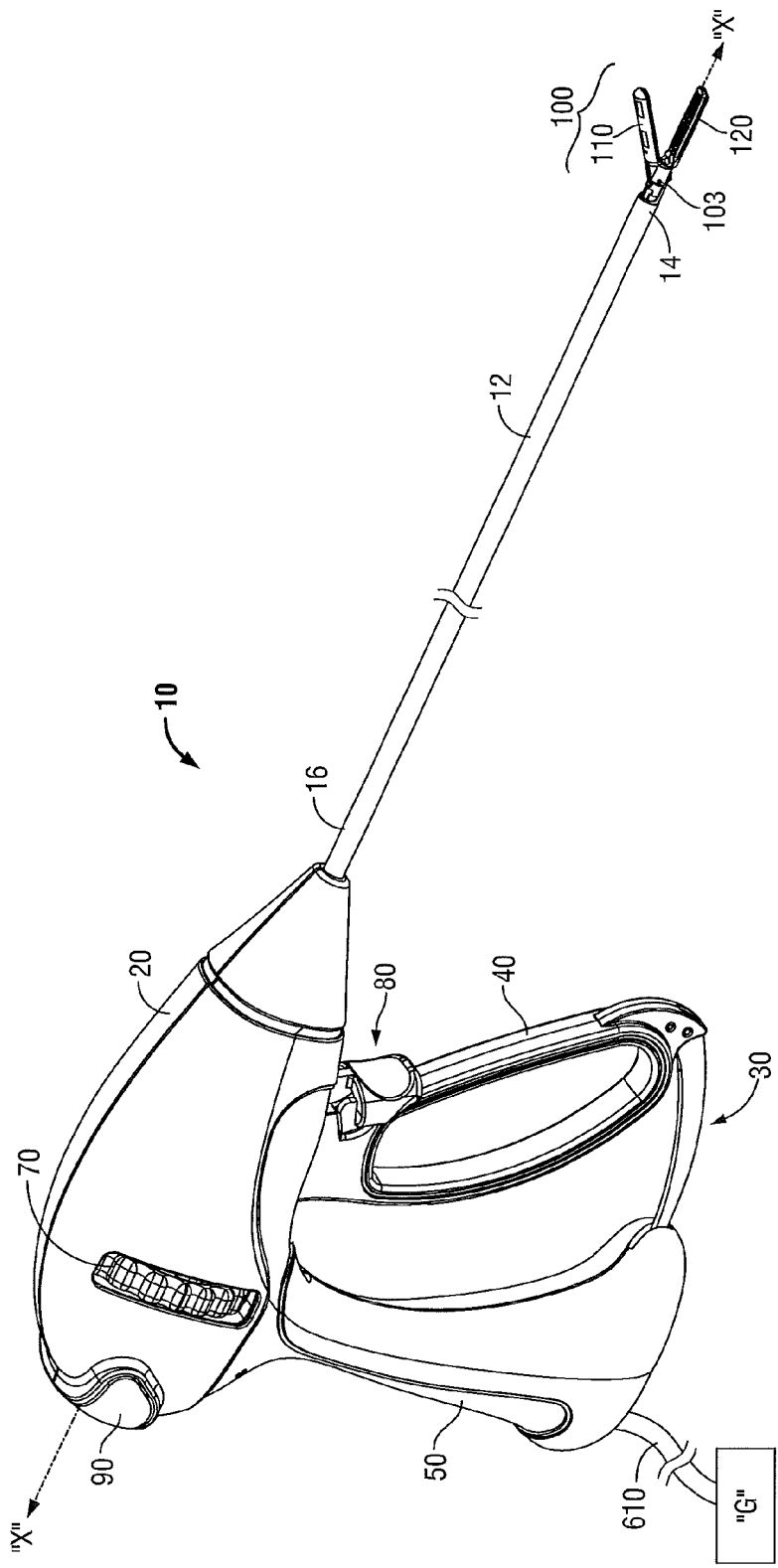
FIG. 1 is a perspective view of a medical device provided in accordance with the present disclosure.
Figure 2:
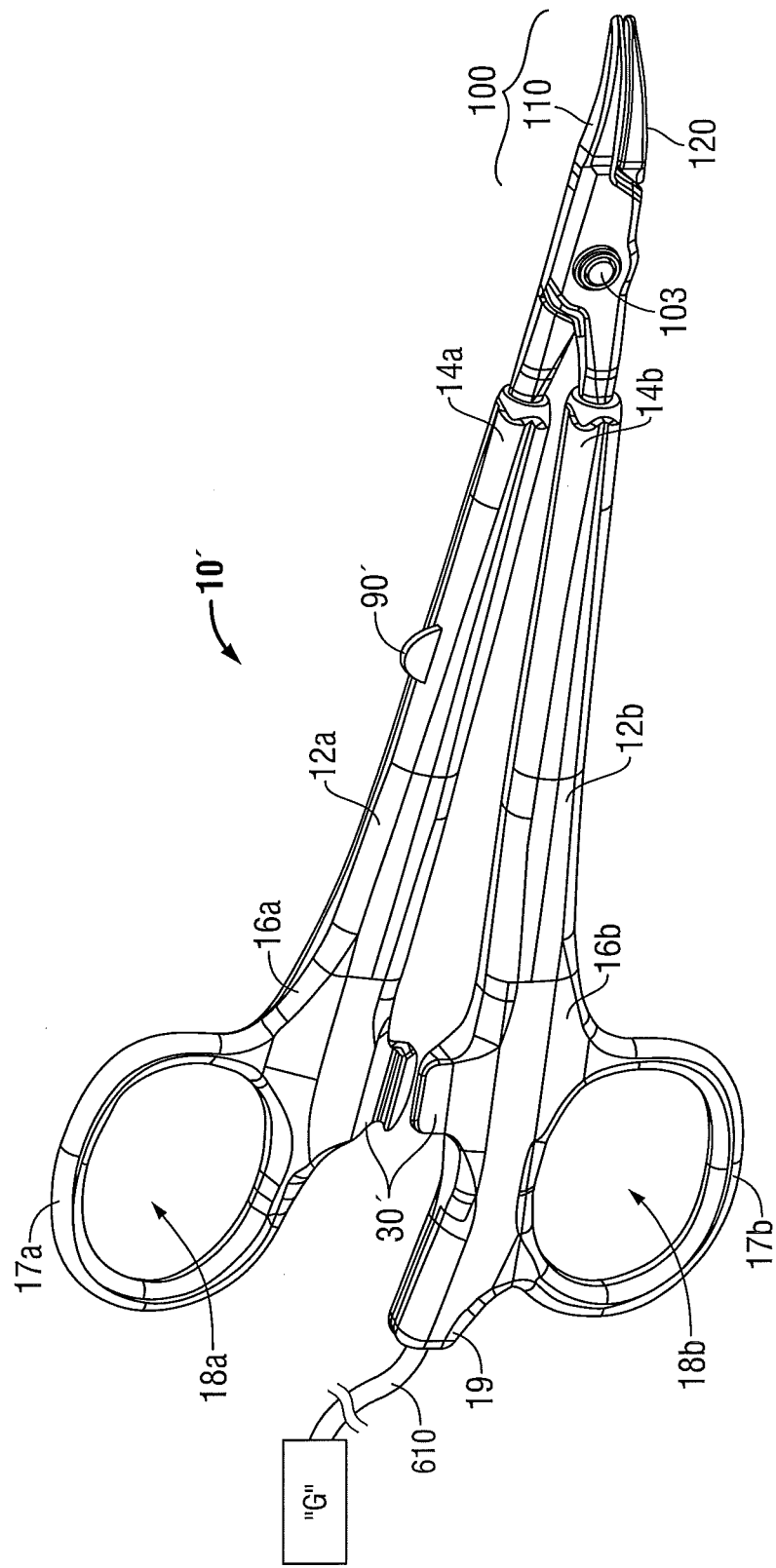
FIG. 2 is a perspective view of a medical device provided in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic device, e.g., forceps 10, an open device, e.g., forceps 10', or any other suitable medical device may be utilized in accordance with the present disclosure. Obviously, different electrical and mechanical connections and considerations apply to each particular type of device, however, the aspects and features of the present disclosure remain generally consistent regardless of the particular device used.

Turning now to FIG. 1, an endoscopic forceps 10 is provided defining a longitudinal axis "X-X" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes cable 610 that connects forceps 10 to a generator "G" or other suitable power source, although forceps 10 may alternatively be configured as a battery-powered device. Cable 610 includes a wire (or wires) (not shown) extending therethrough that has sufficient length to extend through shaft 12 in order to provide electrical energy to at least one of the jaw members 110 and 120 of end effector assembly 100. An activation switch 90 is provide on housing 20 for selectively supplying energy to jaw members 110, 120.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "X-X" to rotate end effector assembly 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of jaw members 110 and 120 includes an opposed electrically conductive tissue-sealing surface 112, 122, respectively (FIG. 3). End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12. End effector assembly 100 will be described in greater detail hereinbelow.

Continuing with reference to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue disposed between tissue-sealing surfaces 112 and 122 (FIG. 3) of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another that, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. It is envisioned that the ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 which is designed to connect the forceps 10' to a source of energy such as a generator "G" (FIG. 1). Proximal shaft connector 19 secures an electrosurgical cable 610' to forceps 10' such that the user may selectively apply energy to the electrically conductive sealing surfaces 112 and 122 (FIG. 3) of jaw members 110 and 120, respectively, as needed. One of the shafts, e.g., shaft 12a, includes an activation switch 90' for selectively supplying energy to jaw members 110, 120.

Turning now to FIG. 3, end effector assembly 100 is shown configured for use with forceps 10 (FIG. 1), although end effector assembly 100 may alternatively be configured for use with forceps 10' (FIG. 2), or any other suitable medical device. As mentioned above, end effector assembly 100 includes first and second jaw members 110, 120 movable relative to one another about a pivot 103 between a spaced-apart position and an approximated position for grasping tissue therebetween. Each jaw member 110, 120 further includes an electrically-conductive tissue-sealing surface 112, 122, respectively. Tissue-sealing surfaces 112, 122 are configured to conduct energy therebetween and through tissue grasped between jaw members 110, 120 to seal tissue, e.g., upon activation of activation switch 90 (FIG. 1) in a tissue-sealing mode of operation.

With continued reference to FIG. 3, each jaw member 110, 120 further includes a longitudinal channel 115, 125 extending therealong and bifurcating the tissue-sealing surface 112, 122, respectively, thereof. The channel of one of the jaw members, e.g., channel 115 of jaw member 110, includes an insulator 117 disposed therein. The channel of the other jaw member, e.g., channel 125 of jaw member 120, includes an electrical cutting member 126 surrounded by an insulator 127 disposed therein. Insulators 117, 127 inhibit electrical cutting member 126 from contacting tissue-sealing surfaces 112, 122 of jaw members 110, 120, respectively. Electrical cutting member 126 is coupled to the source of energy, e.g., generator "G" (FIG. 1), and is configured to conduct energy through tissue and to one or both of tissue-sealing surfaces 112, 122 to electrically cut tissue, e.g., upon activation of activation switch 90 (FIG. 1) in a tissue-sealing mode of operation.

With reference now generally to FIGS. 4A-5E, various embodiments of end effector assemblies of medical devices are shown and described, each including at least one limited-use portion. Generally, the limited-use portion of each of the end effector assemblies is configured to degrade or otherwise transform during use of the medical device such that the medical device is rendered inoperable after a predefined amount of degradation or transformation.

Referring specifically to FIGS. 4A and 4B, as mentioned above, end effector assembly 100 includes first and second jaw members 110, 120, each having a tissue-sealing plate 112, 122 and an insulator 117, 127 disposed within a longitudinal channel 115, 125, respectively. Jaw member 120 further includes an electrical cutting member 126 partially surrounded by insulator 127 and extending towards insulator 117 of jaw member 110. It has been found that, as a by-product of energy transmission during electrical cutting of tissue, e.g., during conduction of energy between electrical cutting member 126 and one or both of tissue-sealing plates 112, 122, insulator 117 may erode at a constant rate. Alternatively or additionally, insulator 117 may be specifically configured to erode, dissolve, or wear down with use at a particular rate or in accordance with a particular function. For example, insulator 117 may be made of a material that erodes from conditions encountered during a surgical procedure, such as, but not limited to, frictional forces encountered during a surgical procedure, chemical reactions with fluids encountered during surgery (water, saline, alcohol, blood, bodily fluids, etc.), or electrical current applied through the material. Insulator 127 of jaw member 120 may also be configured as an eroding insulator 127.

Eroding insulator 117 may include at least one sensor 150 disposed within, on, or in proximity to the insulator 117 such that the sensor 150 can sense a characteristic indicative of erosion of insulator 117. For example, sensor 150 may be configured to detect when electrode 126 comes within a certain distance or contacts with the sensor 150, e.g., via sensing magnetic field, electrical field, electrical current passing from the electrode 126 to the sensor 150, tactile contact with the sensor 150, impedance, a change in capacitance between the electrode 126 and the sensor 150, etc. Sensor 150 may alternatively or additionally be configured to sense any other suitable property or properties of insulator 117, from which a relative amount of erosion of insulator 117 can be determined.

Sensor 150 may be hard-wired or wirelessly connected to a sensing system configured to warn a user and/or prevent further use when a predefined amount of erosion has been determined. For example, sensor 150 may be directly connected to the generator "G" (FIG. 1), and may be configured to relay a signal to the generator "G," which, in turn, ceases outputting electrosurgical energy to end effector assembly 100 when a predetermined amount of erosion has been determined. In such a configuration, generator "G" may include particular features, e.g., hardware and/or software, for determining the amount of erosion of insulator 117 based upon the signal received from sensor 150.

In some embodiments, the insulator 117 may erode until electrical cutting member 126 and insulator 117 no longer maintain a gap distance between seal plates 112, 122, but, rather, allow seal plates 112 and 122 to contact one another and create a brief short circuit scenario. This short circuiting may be sensed by a sensing system (not shown) and the sensing system (not shown) may, as a result of the short circuiting, warn a user and/or prevent further use of the medical instrument. In some embodiments, the generator "G" includes a sensing algorithm for detecting a short circuit and preventing electrical output thereafter. In any case, the safety of the patient is ensured by disallowing damage to the device or tissue as a result of the short circuit scenario because the energy supply may be immediately cut off upon sensing of the short circuit scenario.

Figure 5A:
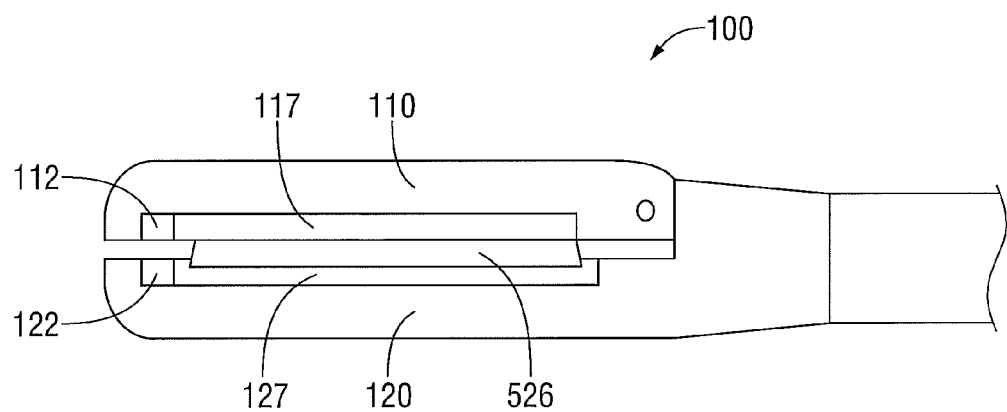
FIG. 5A is a side, cross-sectional view of another end effector assembly provided in accordance with the present disclosure.
Figure 5B:
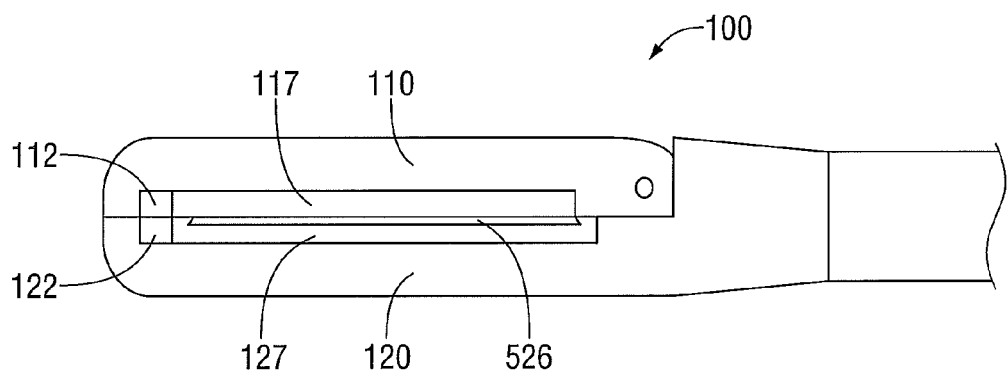
FIG. 5B is a side, cross-sectional view of another end effector assembly provided in accordance with the present disclosure.

In some embodiments, such as that shown in FIGS. 5A-5E, the cutting electrode 526 is configured to erode in a manner similar to the eroding insulator 425 as described above, except that the cutting electrode 526 is made of an eroding conductive material. FIG. 5A shows the electrode 526 before use, and FIG. 5B shows the electrode 526 after erosion. As shown in 5B, electrode 526 may erode until seal plates 112 and 122 contact and create a short circuit scenario. This short circuiting may be sensed by a sensing system (not shown) and the sensing system (not shown) may, as a result of the short circuiting, warn a user and/or prevent further use of the medical instrument. In some embodiments, the generator "G"

includes a sensing algorithm for detecting a short circuit and preventing electrical output thereafter.

Figure 5C:
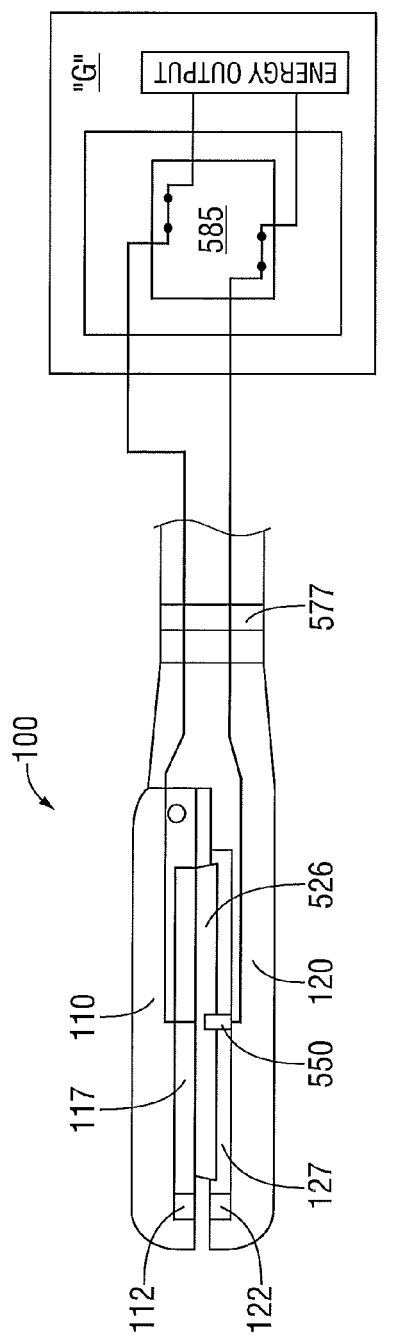
FIG. 5C is a side, cross-sectional view of another end effector assembly provided in accordance with the present disclosure.

Referring to FIG. 5C, end effector assembly 100 may include a sensor 550 disposed within, on, or in proximity to cutting electrode 526. The sensor 550 may be configured to sense a predefined amount of erosion in a manner similar to the sensor 450 as described above. Alternatively, the sensor 550 may be configured to sense gap distance between seal plates 112, 122 when jaw members 110, 120 are disposed in the approximated position. In such a configuration, a short circuit scenario need not occur but, rather, end effector assembly 100 may be rendered inoperable once the gap distance between seal plates 112, 122 falls below a pre-determined threshold.

Figure 5D:
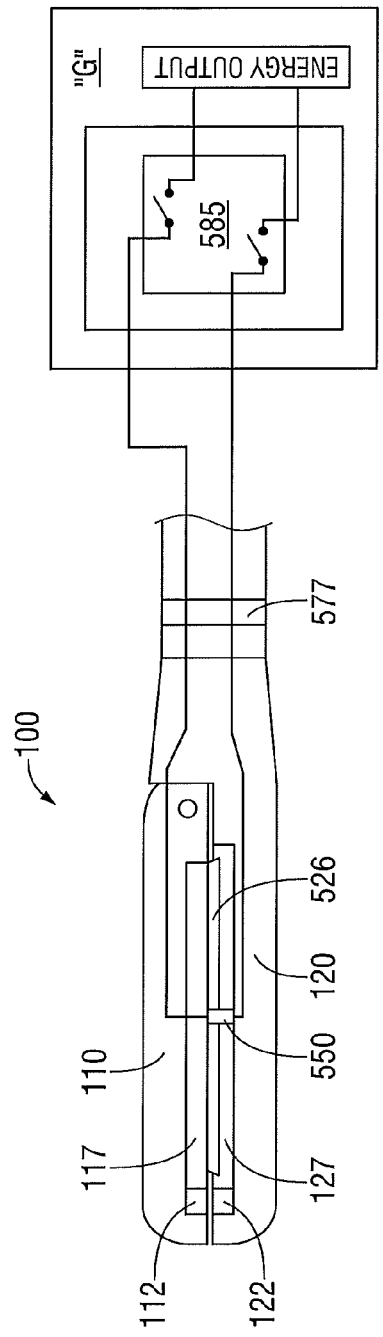
FIG. 5D is a side, cross-sectional view of another end effector assembly provided in accordance with the present disclosure.

In some embodiments, such as that shown in FIGS. 5C and 5D, a sensing system 585 to monitor a quality of the electrode 526 for determining whether to continue to allow end effector assembly 100 to function. As shown in FIG. 5D, when the electrode 526 erodes such that sensor 550 senses a predetermined condition indicative of erosion such as, but not limited to, distance relative to another electrode (seal plates or a separate electrode associated with a separate sensing system), the sensing system 585 may inhibit the supply of electrosurgical energy from generator "G" or other suitable energy source, thus inhibiting further use of end effector assembly 100.

Sensing system 585 may be implemented via any suitable hardware and software components. In particular, sensing system 585 may include a computer implemented algorithm, analog electrical circuit, or combination of analog electrical circuits/microprocessor based circuitry. Sensing system 585 may be included in the generator "G" as shown, or may be separate therefrom.

Figure 5E:
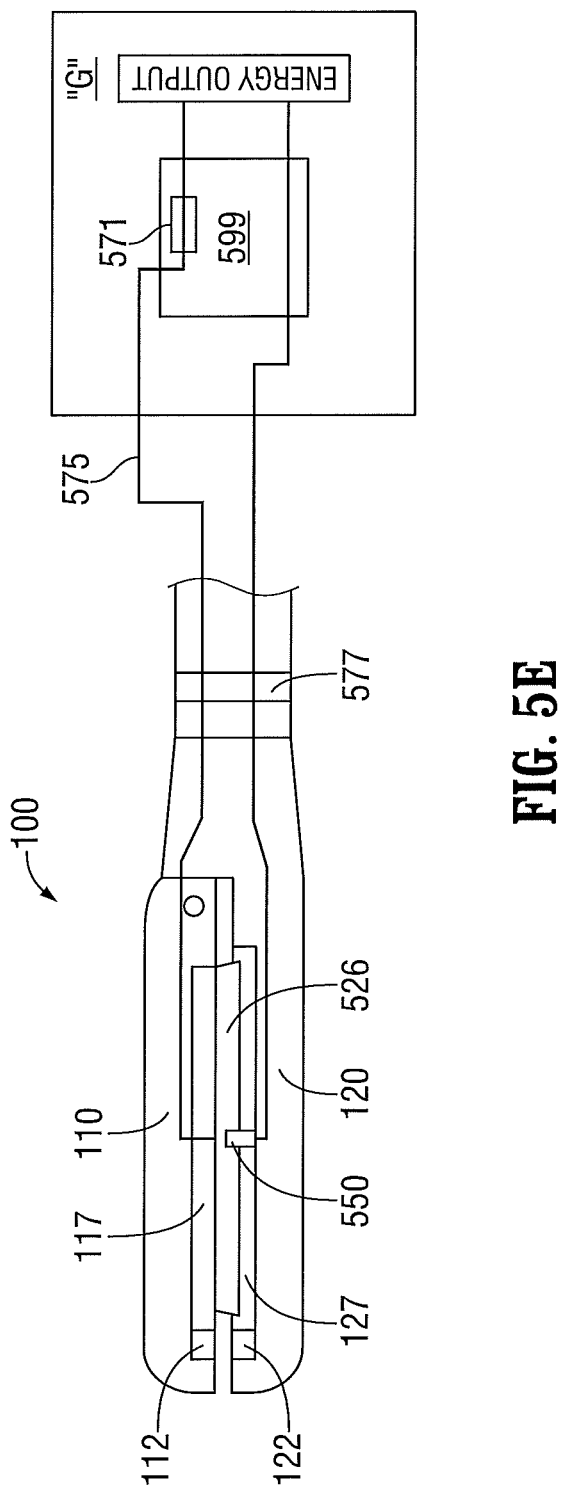
FIG. 5E is a side, cross-sectional view of another end effector assembly provided in accordance with the present disclosure.

Referring to FIG. 5E, an embodiment of a sensing system 599 is shown. As shown, system 599 includes a short circuit fuse 571 that is connected in series between the source of energy and end effector assembly 100. Connected to fuse 571 is fuse reset device 575. Fuse reset device 575 may be a mechanical, electro-mechanical, electrical, or any other device capable of resetting fuse 571. Fuse reset device 575 is connected to an attachment portion 577 that attaches the end effector assembly 100 to the rest of the medical device.

When the electrode 526 erodes and short circuiting occurs, fuse 571 is tripped preventing any further energy from being transfer to end effector assembly 100. Only when the end effector assembly 100 is removed and replaced, or when a new instrument with a new end effector assembly 100 is connected to the electrosurgical generator, will the fuse resetting device 575 trigger resetting of fuse 571 and enable further use of end effector assembly 100. Alternatively, fuse 571 may be disposed on or within the end effector assembly 100 such that when the insulator 427 or electrode 526 erodes a predetermined amount, the fuse 571 permanently breaks, requiring replacement of the end effector assembly 100.

The sensing systems described herein may be included in generator "G" and be implemented through, and integrated with, any suitable generator control software/hardware. For example, the generator control software may be ForceTriad™ software sold by Covidien, LP.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A medical device, comprising:
    an end effector assembly configured to conduct energy through tissue to treat tissue, the end effector assembly including a first selectively-energizable electrode, a second selectively-energizable electrode, and an insulator configured to insulate the first and second selectively-energizable electrodes from one another, wherein the insulator is configured to degrade during use; and
    a control system configured to monitor degradation of the insulator.

2. The medical device of claim 1, wherein the control system includes a sensor configured to sense at least one characteristic indicative of degradation of the insulator and to provide a signal representative of the at least one characteristic sensed.

3. The medical device of claim 1, wherein the insulator is configured to degrade as a result of energy conduction therethrough or adjacent thereto.

4. The medical device of claim 1, wherein the control system monitors the insulator such that when the insulator degrades to a predetermined threshold, the control system inhibits energy transmission to the end effector assembly.

5. The medical device of claim 4, wherein, the predetermined threshold occurs prior to the point at which the insulator degrades sufficiently so as to short-circuit the end effector assembly.

6. A method, comprising:
    conducting energy from a first selectively-energizable electrode of an end effector assembly, through tissue, to a second selectively-energizable electrode of the end effector assembly to treat the tissue, wherein the first and second selectively-energizable electrodes are separated by an insulator configured to degrade during use; and
    monitoring degradation of the insulator.

7. The method of claim 6, wherein monitoring degradation further includes sensing at least one characteristic indicative of degradation of the insulator.

8. The method of claim 6, further comprising inhibiting energy transmission to the end effector assembly when degradation of the insulator exceeds a pre-determined threshold.

9. The method of claim 8, wherein the predetermined threshold occurs prior to the point at which the insulator degrades sufficiently so as to short-circuit the end effector assembly.

* * * * *